US008536104B1

(12) United States Patent
Roman-Barcelo

(10) Patent No.: US 8,536,104 B1
(45) Date of Patent: Sep. 17, 2013

(54) HAND SOAP BAR WITH TETHER

(71) Applicant: Hector Roman-Barcelo, Miami, FL (US)

(72) Inventor: Hector Roman-Barcelo, Miami, FL (US)

( * ) Notice: Subject to any disclaimer, the term of this patent is extended or adjusted under 35 U.S.C. 154(b) by 0 days.

(21) Appl. No.: 13/669,205

(22) Filed: Nov. 5, 2012

(51) Int. Cl.
*A61K 8/00* (2006.01)

(52) U.S. Cl.
USPC ................................ 510/141; 510/146; 401/8

(58) Field of Classification Search
USPC .......................................................... 510/141
See application file for complete search history.

(56) References Cited

U.S. PATENT DOCUMENTS

| | | | |
|---|---|---|---|
| 1,787,660 A * | 1/1931 | Blakeley | 401/8 |
| 2,243,634 A | 5/1941 | Kadish | |
| 6,799,917 B1 | 10/2004 | Sampson | |
| 2005/0095056 A1 | 5/2005 | King | |

* cited by examiner

*Primary Examiner* — Necholus Ogden, Jr.
(74) *Attorney, Agent, or Firm* — Richard C. Litman

(57) ABSTRACT

The hand soap bar with tether is a bar of hand soap having a built-in tether. The tether includes an elastic band that can be attached to a user's wrist. An anchor member is encased in the soap bar. One end of the tether is attached to the anchor member. An elastic loop defines the other end of the tether.

3 Claims, 3 Drawing Sheets

HAND SOAP BAR WITH TETHER

BACKGROUND OF THE INVENTION

1. Field of the Invention

The present invention generally relates to personal hygiene products, and particularly to a hand soap bar with tether for handling and controlling a wet bar of hand soap.

2. Description of the Related Art

Controlling a wet bar of hand soap is relatively difficult, even for persons having high degrees of dexterity. For children, elderly people, handicapped, people, etc., the task of preventing the slippery soap bar from falling to the floor of the shower or floating out of reach in the bath water is much more difficult. Bending or stooping to retrieve a dropped soap bar has been the cause of many falls that have produced some serious injuries, and even some fatalities. Many devices have been proposed to aid users in maintaining control of a slippery soap bar. Unfortunately, these devices have proven to be cumbersome and less than satisfactory in use. The art would certainly welcome a device that would facilitate handling a slippery soap bar to prevent a user, especially children and the infirm, from accidentally dropping the soap bar. Thus, a hand soap bar with tether solving the aforementioned problems is desired.

SUMMARY OF THE INVENTION

The hand soap bar with tether is drawn to a bar of hand soap having a built-in tether. The tether includes an elastic band that can be attached to a user's wrist. An anchor member is encased in the soap bar. One end of the tether is attached to the anchor member. An elastic loop defines the other end of the tether.

Accordingly, the invention presents a device that allows a user to handle and maintain control of a soap bar while bathing or showering. The device is designed for quick and easy attachment to the user's wrist. The invention provides for improved elements thereof in an arrangement for the purposes described that are inexpensive, dependable and fully effective in accomplishing their intended purposes.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
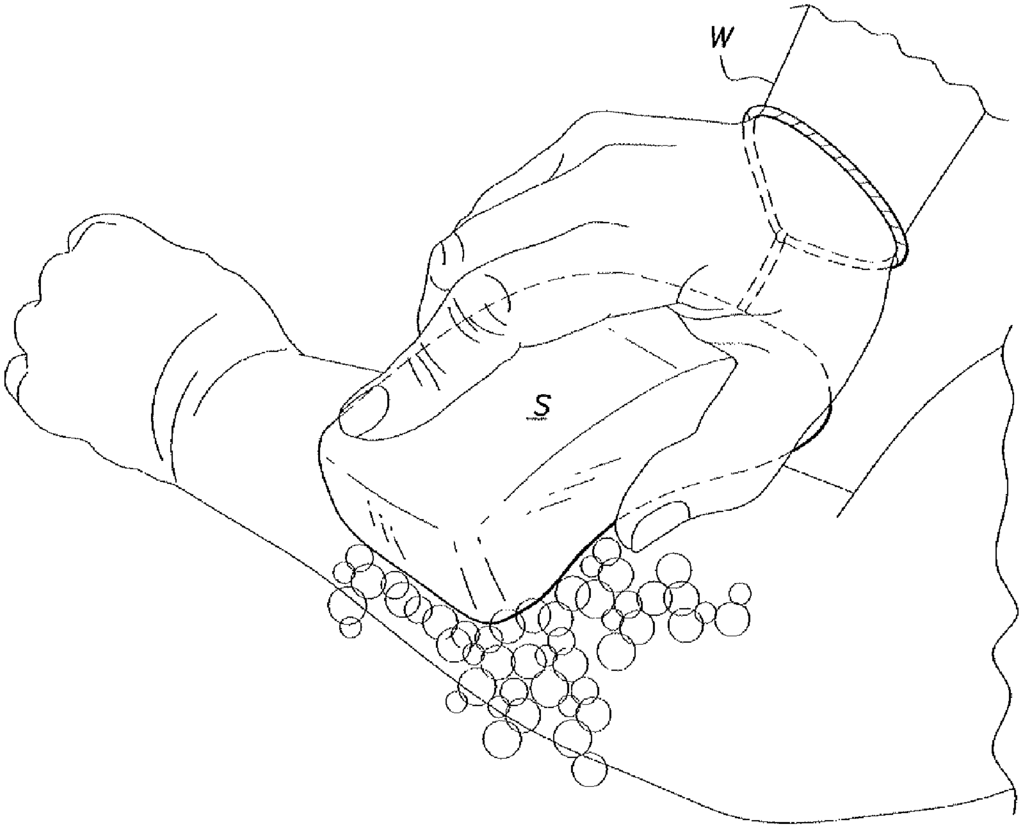
FIG. 1 is an environmental, perspective view of a hand soap bar with tether according to the present invention.
Figure 2:
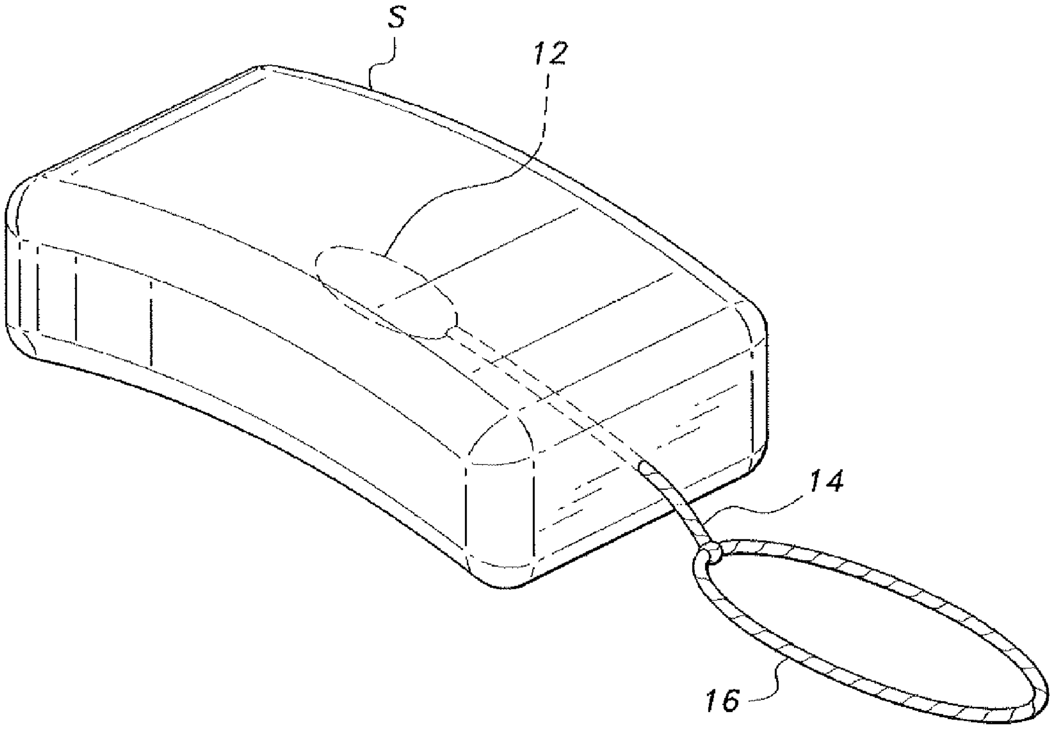
FIG. 2 is a perspective view of a hand soap bar with tether according to the present invention.
Figure 3:
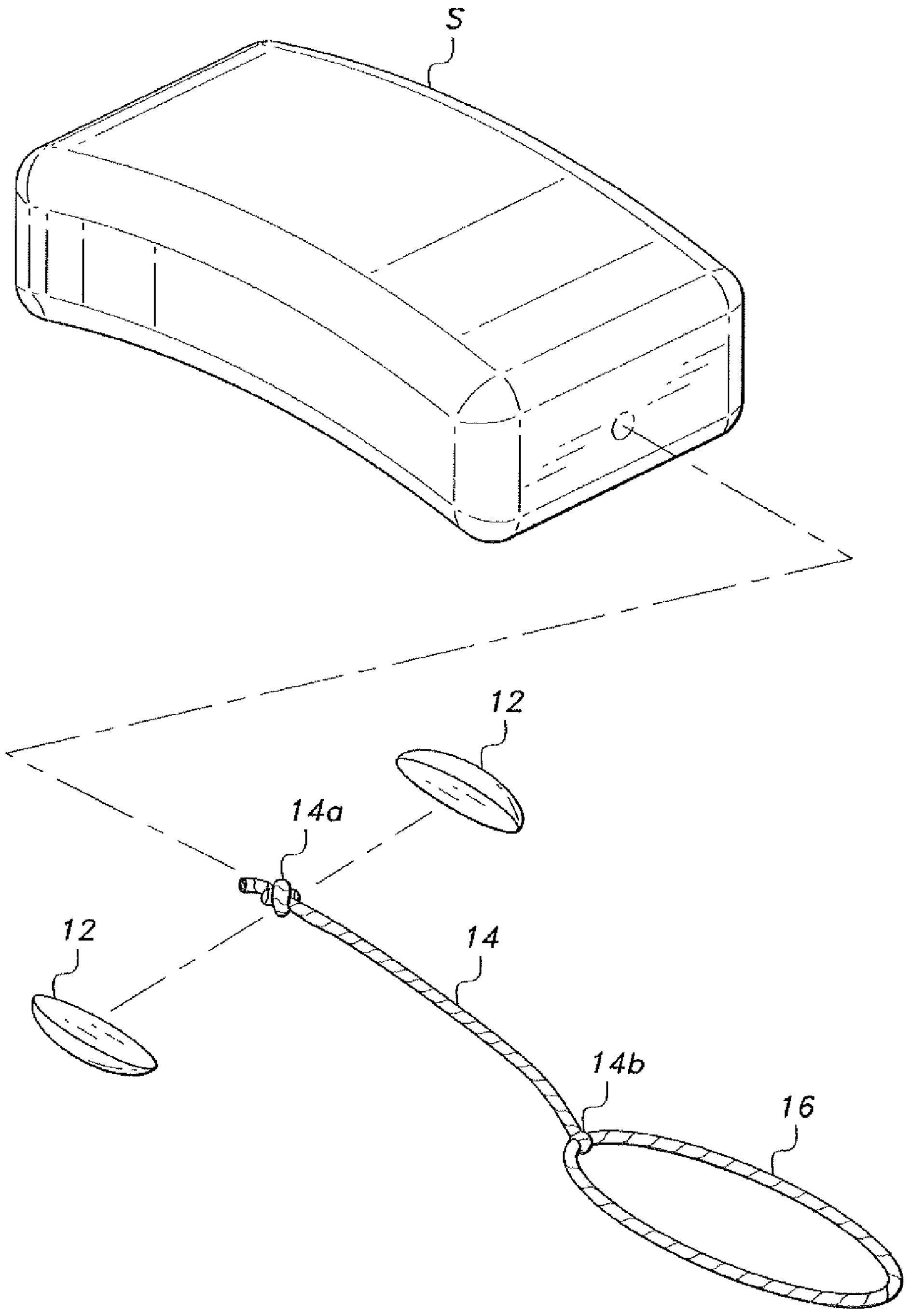
FIG. 3 is an exploded, perspective view of a hand soap bar with tether according to the present invention.

With reference to FIGS. 1-3, the hand soap bar with tether secures a soap bar S to the wrist W of a user. The tether comprises an anchor 12, an elongate cord 14 and a loop 16. One end 14*a* of the cord 14 is firmly attached to the anchor 12. The other end 14*b* of the cord 14 is firmly attached to a loop member 16. Any suitable means of attachment may be made to attach the anchor 12 and the loop 16 to the cord 14. Although preferably fabricated from a plastic material, it should be noted that the anchor 12 may be fabricated from any suitable material (wood, metal, rubber, etc.). The cord 14 is fabricated from flexible material, such as nylon, rayon, cotton, or the like. The loop 16 is fabricated from a suitable elastic material so that it may expand to easily slip over the hand and contract to loosely fit around the wrist.

The tether device is incorporated into the soap bar S during the soap bar manufacturing process. The anchor 12 and the cord end 14*a* attached thereto is encapsulated in the soap bar S. The cord 14 extends exteriorly of the soap bar S and the elastic loop 16 is attached thereto. This construction permits a user to securely attach the soap bar S to his/her wrist W and prevents the bar from falling or floating away.

It is to be understood that the present invention is not limited to the embodiments described above, but encompasses any and all embodiments within the scope of the following claims.

I claim:

1. A tethered soap bar, consisting of:

a bar of soap;

an anchor member encapsulated in the bar of soap;

an elongate, inelastic flexible cord having one end attached to the anchor member and extending from the bar of soap and an opposite free end; and an elastic continuous loop member attached to the free end of the cord exterior to the bar of soap.

2. The tethered soap bar according to claim 1, wherein said anchor is fabricated from a plastic material.

3. The tethered soap bar according to claim 1, wherein said inelastic, flexible cord is made of a material selected from the group consisting of nylon, rayon, and cotton.

* * * * *